(12) United States Patent
Schwab

(10) Patent No.: US 9,693,809 B2
(45) Date of Patent: Jul. 4, 2017

(54) SPINAL CORRECTION IMPLANT SYSTEM AND METHOD

(71) Applicant: Warsaw Orthopedic, Inc., Warsaw, IN (US)

(72) Inventor: Frank J. Schwab, New York, NY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 272 days.

(21) Appl. No.: 14/221,051

(22) Filed: Mar. 20, 2014

(65) Prior Publication Data
US 2015/0265316 A1 Sep. 24, 2015

(51) Int. Cl.
*A61B 17/70* (2006.01)
*A61B 90/00* (2016.01)

(52) U.S. Cl.
CPC ...... *A61B 17/7053* (2013.01); *A61B 17/7002* (2013.01); *A61B 2090/0811* (2016.02); *A61B 2090/392* (2016.02); *A61B 2090/3937* (2016.02)

(58) Field of Classification Search
CPC ... A61B 17/7053; A61B 17/82; A61B 17/823; A61B 17/826; A61B 17/842; A61B 17/0487; A61B 17/8861; A61B 17/8869
See application file for complete search history.

(56) References Cited

U.S. PATENT DOCUMENTS

| | | | | |
|---|---|---|---|---|
| 874,417 A * | 12/1907 | Moss | ...................... | F16G 11/00 403/209 |
| 1,825,074 A * | 9/1931 | Knapp | ................... | F16G 11/00 24/132 R |
| 4,156,574 A * | 5/1979 | Boden | ..................... | F16G 11/10 24/115 M |
| 4,379,358 A * | 4/1983 | Wibrow | .................. | F16G 11/00 24/115 M |
| 4,455,717 A * | 6/1984 | Gray | ....................... | F16G 11/14 24/115 M |
| 5,078,731 A * | 1/1992 | Hayhurst | ............ | A61B 17/0487 606/151 |
| 5,584,835 A * | 12/1996 | Greenfield | ......... | A61B 17/0401 606/232 |
| 5,702,397 A * | 12/1997 | Goble | ................ | A61B 17/0401 606/232 |
| 6,086,608 A * | 7/2000 | Ek | ....................... | A61B 17/0487 606/232 |
| 6,200,329 B1 * | 3/2001 | Fung | .................. | A61B 17/0487 606/232 |
| 6,260,241 B1 * | 7/2001 | Brennan | ................. | F16G 11/00 24/115 K |
| 6,641,584 B2 * | 11/2003 | Hashimoto | ........ | A61B 17/7022 606/263 |
| 7,090,690 B2 * | 8/2006 | Foerster | ............. | A61B 17/0401 606/232 |
| 7,879,072 B2 * | 2/2011 | Bonutti | .............. | A61B 17/0487 606/232 |
| 8,057,472 B2 * | 11/2011 | Walker | ............... | A61B 17/7016 128/898 |
| 8,202,295 B2 * | 6/2012 | Kaplan | .............. | A61B 17/0401 606/232 |

(Continued)

*Primary Examiner* — Lynnsy Summitt

(57) ABSTRACT

A spinal implant detection device comprises at least one detectable marker connected to an implantable longitudinal element and including a capture element configured to facilitate manipulation of the longitudinal element. Systems and methods are disclosed.

21 Claims, 6 Drawing Sheets

(56) References Cited

U.S. PATENT DOCUMENTS

| | | | |
|---|---|---|---|
| 8,407,067 B2* | 3/2013 | Uthgenannt | A61F 2/30942 |
| | | | 623/20.35 |
| 2004/0127907 A1* | 7/2004 | Dakin | A61B 17/842 |
| | | | 606/62 |
| 2006/0293690 A1* | 12/2006 | Abdelgany | A61B 17/7086 |
| | | | 606/103 |
| 2008/0288070 A1* | 11/2008 | Lo | A61B 17/0401 |
| | | | 623/13.14 |
| 2010/0324692 A1* | 12/2010 | Uthgenannt | A61F 2/30942 |
| | | | 623/20.35 |
| 2011/0245875 A1* | 10/2011 | Karim | A61B 17/7037 |
| | | | 606/263 |
| 2011/0301644 A1* | 12/2011 | Belliard | A61B 17/7008 |
| | | | 606/263 |
| 2012/0130373 A1* | 5/2012 | Larroque-Lahitette | A61B 17/7001 |
| | | | 606/74 |
| 2015/0289911 A1* | 10/2015 | Beyar | A61B 17/7059 |
| | | | 606/70 |

* cited by examiner

SPINAL CORRECTION IMPLANT SYSTEM AND METHOD

TECHNICAL FIELD

The present disclosure generally relates to medical devices for the treatment of musculoskeletal disorders, and more particularly to a surgical system and a method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including abnormal growth or development of structures, trauma, disease and degenerative conditions caused by injury and aging. Spinal disorders can lead to deformity, cosmetic and functional impairment and symptoms including pain, nerve damage, and partial or complete loss of mobility.

Non-surgical treatments, such as medication, rehabilitation and exercise can be effective, however, may fail to address deformity or relieve the symptoms associated with these disorders. Surgical treatment of these spinal disorders includes correction fusion, fixation, discectomy, laminectomy and implantable prosthetics. Correction treatments used for positioning and alignment may employ implants such as rods, tethers and bone screws for stabilization of a treated section of a spine. This disclosure describes an improvement over these prior art technologies.

SUMMARY

In one embodiment, a spinal implant detection device is provided. The spinal implant detection device comprises at least one detectable marker connectable to an implantable longitudinal element and including a capture element configured to facilitate manipulation of the longitudinal element. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
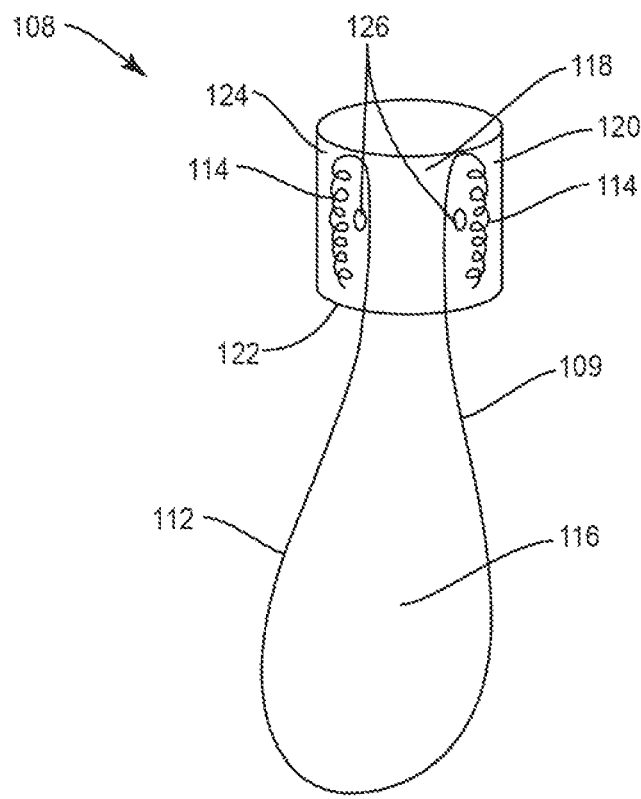
FIG. 1 is a perspective view of components of one embodiment of a system in accordance with the principles of the present disclosure.

The exemplary embodiments of the system and related methods of use disclosed are discussed in terms of medical devices for the treatment of musculoskeletal disorders and more particularly, in terms of a surgical system and method for treatment of a spine disorder. In one embodiment, the present disclosure provides a surgical system and method that release tension and/or excessive or over correction of an implanted correction system, which is employed to treat a spine disorder, as described herein. This configuration can avoid non-desirable surgery, such as, for example, a thoracotomy and/or tissue disruption or damage. See also, the examples and disclosure of systems and methods shown and described in U.S. patent application Ser. No. 14/221,037 filed Mar. 20, 2014, and published as U.S. Patent Application Publication No. 2015/0265303 A1, on Sep. 24, 2015, the entire contents of which being incorporated herein by reference.

In some embodiments, the present system can be employed with a method and/or procedure, such as, for example, an index correction surgery for treating a spine disorder, such as, for example, those described herein, and includes an implantable device to facilitate tether release, for example, during a subsequent procedure. In some embodiments, the device can be looped around, or attached to a tether and detectable and/or readily findable, for example, from a posterior approach using medical imaging, as described herein. In some embodiments, the method can include the steps of finding the tether with the device and releasing tension in the tether.

In some embodiments, the present system includes a tether cutting system such that during the index surgery, the device includes a looped configuration that is passed around a tether and the device includes a tail passed to a posterior spinal space for capture in a present and/or subsequent procedure. In one embodiment, the loop defines a passage for disposal of the tether. In one embodiment, the device includes a cap and a loop. In one embodiment, the system includes a capture device, a tether and an anchor. In one embodiment, the system includes a head instrument having a pair of tongs that capture a device having a cap and a loop. In one embodiment, the cap includes an extra length of loop material such that pulling on the cap against the loop, which is held by the tether, permits additional loop material to uncoil and the cap can be displaced.

In one embodiment, the device includes a housing and/or enclosure that can be passed around a tether during the index surgery. In one embodiment, a set of strings, or ligaments are passed to a posterior spine space, such as, for example, a costovertebral space. In one embodiment, at the time of tether release, the strings/ligament are easlily found and a cutting surface employed to release tension in the tether.

In some embodiments, the system and method employ a substantially posterior surgical approach and/or variation thereof and creates a substantially posterior surgical pathway to dispose a surgical instrument to engage components of an implanted correction system to release tension and/or avoid excessive or over correction. In some embodiments, the system releases tension in the components after a substantially desired correction and/or alignment has been achieved and/or tension becomes too great. For example, the system can be employed in cases, such as, a spinal tethering system that has been implanted with a child for several months or years and the maximum possible straightening has been applied to a scoliotic spine.

In one embodiment, a medical practitioner approaches an anterior tethering system from a posterior surgical approach. In one embodiment, the tethering system is cut to release tension in a selected tether. In some embodiments, the system is employed with a percutaneous surgical procedure, which may include a dilator. In one embodiment, the system is employed with a procedure that penetrates soft tissue and avoids a transverse process adjacent a selected region of a tether to be cut. In some embodiments, the system is employed with image guidance, such as, for example, fluoroscopy or CT scanning.

In one embodiment, the system includes a dilator that is inserted adjacent a surgical site such that a cutting instrument can be disposed adjacent the selected region of the tether. In some embodiments, the dilator creates a posterior surgical pathway. In one embodiment, the practitioner positions a cutting tool through the surgical pathway such that a cutting surface is disposed adjacent to a spinal tethering system. In one embodiment, the cutting tool extends out of a cannula during a percutaneous procedure and the cutting tool cuts the tether to release tension in the tether. In one embodiment, the cutting tool is positioned around or through a transverse process. In some embodiments, the system comprises a cutting surface that includes a metallic wire that is heated. In some embodiments, the wire is inserted through a cannula to reach the location of the tether. In some embodiments, the cutting surface can extend out of the cannula and cut the tether. In some embodiments, the cutting surface captures the tether with the cannula such that the cannula is a fixed surface and the cutting surface cuts the tether with an edge of the cannula.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, vessels, ligaments, tendons, cartilage and/or bone unless specifically referred to otherwise.

The following discussion includes a description of a surgical system including surgical instruments, related components and methods of employing the system in accordance with the principles of the present disclosure. Alternate embodiments are also disclosed. Reference is made in detail to the exemplary embodiments of the present disclosure, which are illustrated in the accompanying figures. Turning to FIGS. 1-4, there are illustrated components of a method and system, such as, for example, a surgical correction system 10 in accordance with the principles of the present disclosure.

The components of system 10 can be fabricated from biologically acceptable materials suitable for medical applications, including metals, synthetic polymers, ceramics and bone material and/or their composites. For example, the components of system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers inducting polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

Figure 2:
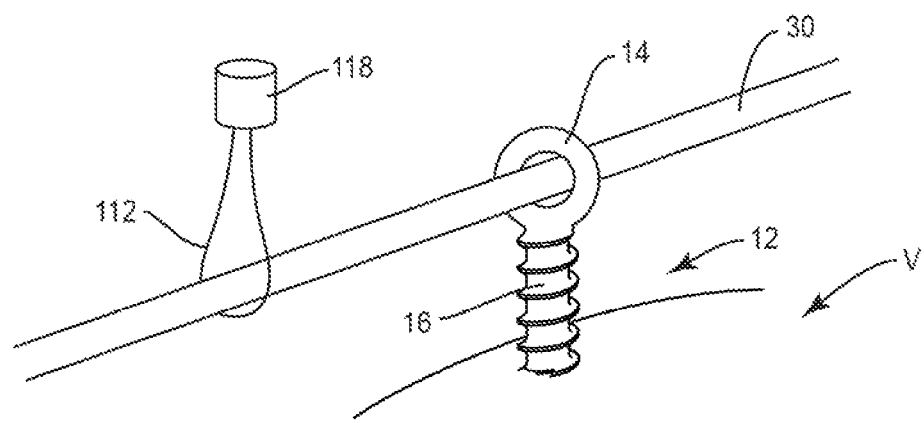
FIG. 2 is a perspective view of components of one embodiment of a system in accordance with the principles of the present disclosure disposed with vertebrae.

A spinal construct including, such as, for example, a tissue fastener, such as, for example, a bone screw 12 is fixed with vertebrae V, as shown in FIG. 2. In some embodiments, system 10, which may include the spinal construct, and/or the spinal construct may include one or a plurality of tissue fasteners. In some embodiments, one or more of bone screws 12 may be engaged with tissue in various orientations, such as, for example, series, parallel, offset, staggered and/or alternate vertebral levels. In some embodiments, one or more tissue fasteners may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, dips, snaps, friction fittings, compressive fittings, expanding rivets, staples, nails, adhesives, posts, fixation plates and/or posts.

Bone screw 12 comprises a first portion, such as, for example, a head 14 and a second portion, such as, for example, an elongated shaft 16 configured for penetrating tissue. Head 14 includes a receiving portion configured for disposal of an implant, such as, for example, a tether 30. The spinal construct includes a longitudinal element, such as, for example, tether 30. Tether 30 is attached with and extends along an anterior portion of vertebrae V.

The spinal construct forms one or more components of a correction treatment and/or correction system used for positioning and alignment for stabilization of a treated section of vertebrae V, which is implanted with vertebrae V in a prior surgical procedure. In some embodiments, system 10 may be employed with a surgical procedure for implanting components of the correction system. In one embodiment, tether 30 is connected with heads 14 of bone screws 12 causing a tension in tether 30 and/or vertebrae V. In some embodiments, the spinal construct, for example, tether 30 and/or a tension thereof is employed to displace, pull, twist or align vertebrae V as part of a correction system and treatment.

In some embodiments, tether 30 has a flexible configuration, which includes movement in a lateral or side to side direction and prevents expanding and/or extension in an axial direction upon fixation with vertebrae. In some embodiments, all or only a portion of tether 30 may have a semi-rigid, rigid, flexible or elastic configuration, and/or have elastic and/or flexible properties such as the elastic and/or flexible properties corresponding to the material examples described above such that tether 30 provides a selective amount of expansion and/or extension in an axial direction. Tether 30 can include a plurality of separately attachable or connectable portions or sections, such as bands or loops, or may be monolithically formed as a single continuous element.

Tether 30 has an outer surface 32 and a uniform thickness/diameter. In some embodiments, outer surface 32 may have various surface configurations, such as, for example, rough, threaded for connection with surgical instruments, arcuate, undulating, porous, semi-porous, dimpled, polished and/or textured. In some embodiments, the thickness defined by tether 30 may be uniformly increasing or decreasing, or have alternate diameter dimensions along its length. In some embodiments, tether 30 may have various cross section configurations, such as, for example, oval, oblong, triangular, rectangular, square, polygonal, irregular, uniform, non-uniform, variable and/or tapered.

In some embodiments, tether 30 may have various lengths. In some embodiments, tether 30 may be braided, such as a rape, or include a plurality elongated elements to provide a predetermined force resistance. In some embodiments, tether 30 may be made from autograft and/or allograft and be configured for resorbable or degradable applications. In some embodiments, the longitudinal element can include a spinal rod.

System 10 includes a detectable marker 108, as shown in FIG. 1. Detectable marker 108 includes an elongate element, such as, for example, a string 109. String 109 includes ends 114 that are configured to form a loop 112. Loop 112 is configured for disposal about tether 30. In one embodiment, the elongate element includes a wire. Loop 112 is configured to form an opening 116 configured for disposal of tether 30. In one embodiment, opening 116 is expandable to facilitate disposal of various sized tethers 30.

In some embodiments, string 109 has a flexible configuration, which includes movement in a lateral or side to side direction and prevents expanding and/or extension in an axial direction upon disposal with tether 30. In some embodiments, all or only a portion of string 109 may have a semi-rigid, rigid, flexible or elastic configuration, and/or have elastic and/or flexible properties such as the elastic and/or flexible properties corresponding to the material examples described above such that string 109 provides a selective amount of expansion and/or extension in an axial direction of loop 112. String 109 can include a plurality of separately attachable or connectable portions or sections, such as bands or loops, or may be monolithically formed as a single continuous element.

String 109 is connected with a capture element 118 at ends 114. Capture element 118 includes a housing 120 having an inner surface 122 configured to connect with ends 114. In one embodiment, capture element 118 may include mating elements such as, for example, dips, hooks, adhesives, spring loaded buttons and/or flanges to connect with ends 114. Housing 120 includes an outer surface 124 configured to mate with a surgical instrument, as discussed herein. Surface 124 includes at least one cavity such as, for example, mating cavities 126 configured for engagement with the surgical instrument to facilitate capture of capture element 118. In one embodiment, ends 114 include a reservoir of loop material disposed with capture element 118 such that loop 112 is expandable.

Figure 3:
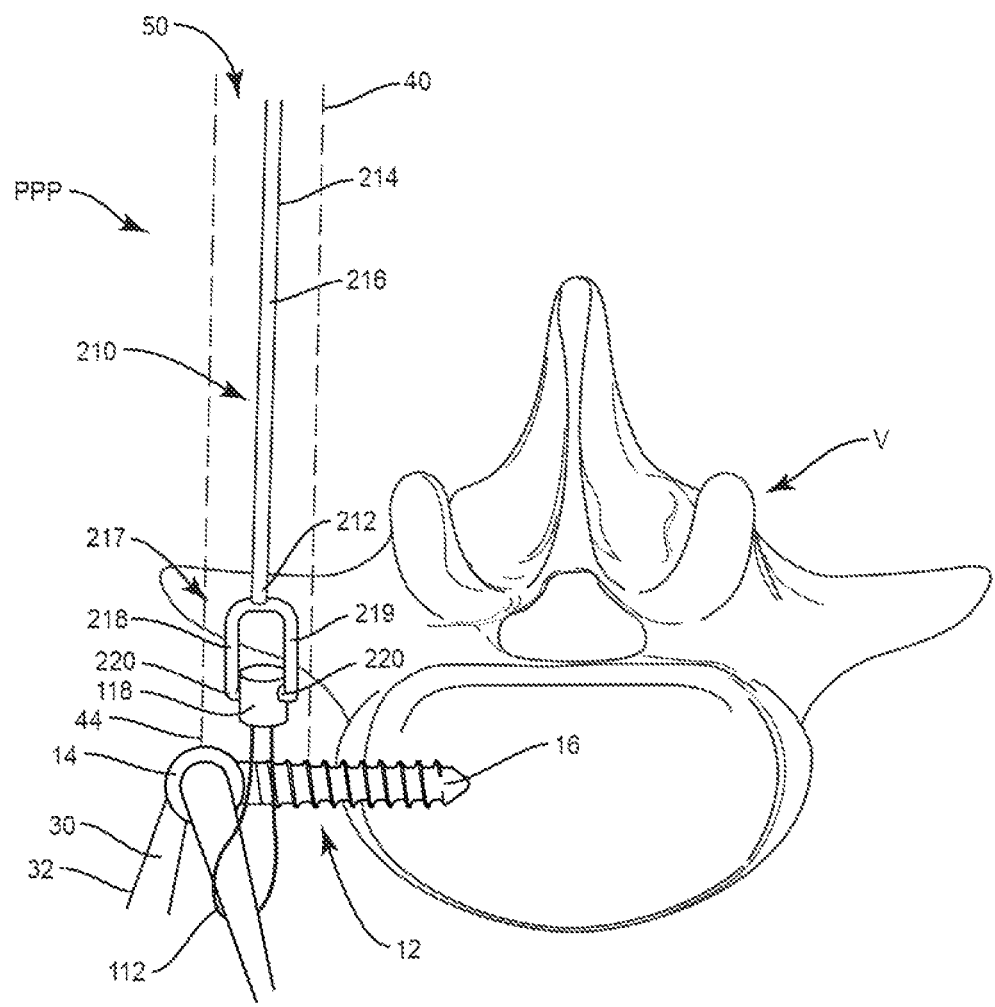
FIG. 3 is an axial view of components, part in phantom, of one embodiment of a system in accordance with the principles of the present disclosure disposed with vertebrae.

As shown in FIG. 3, capture element 118 is engageable with the surgical instrument, such as, for example, a gripper 210. Gripper 210 includes an elongated portion 216 extending between a distal end 212 and a proximal end 214. End 212 includes a gripping portion 217 having arms 218, 219. Arms 218, 219 are configured to grasp capture element 118. In one embodiment, arms 218, 219 are rotatable and/or pivotable relative to one another and movable between an expanded configuration to release capture element 118 and a contracted configuration to engage and capture element 118. In one embodiment, arms 218, 219 include extensions 220 configured to mate with mating cavities 126. In one embodiment, elongated portion 216 includes an inner surface defining a passageway. The passageway is configured for disposal of a mechanical linkage for manipulating arms 218, 219 for capture of capture element 118, as discussed herein.

In same embodiments, system 10 includes one or a plurality of detectable markers. In some embodiments, the detectable marker can include indicia comprising identifying information relating to one or more of the detectable marker, tether 30, a patient being treated and/or a medical procedure. In some embodiments, the indicia includes a memory device or data carrier, such as, for example, a RFID tag used in conjunction with an RFID system. In some embodiments, the indicia includes visual indicia, such as, for example, a label, color coding, numbers or an icon. In some embodiments, the indicia includes tactile indicia, such as, for example, raised portions, dimples and/or texturing.

Figure 5:
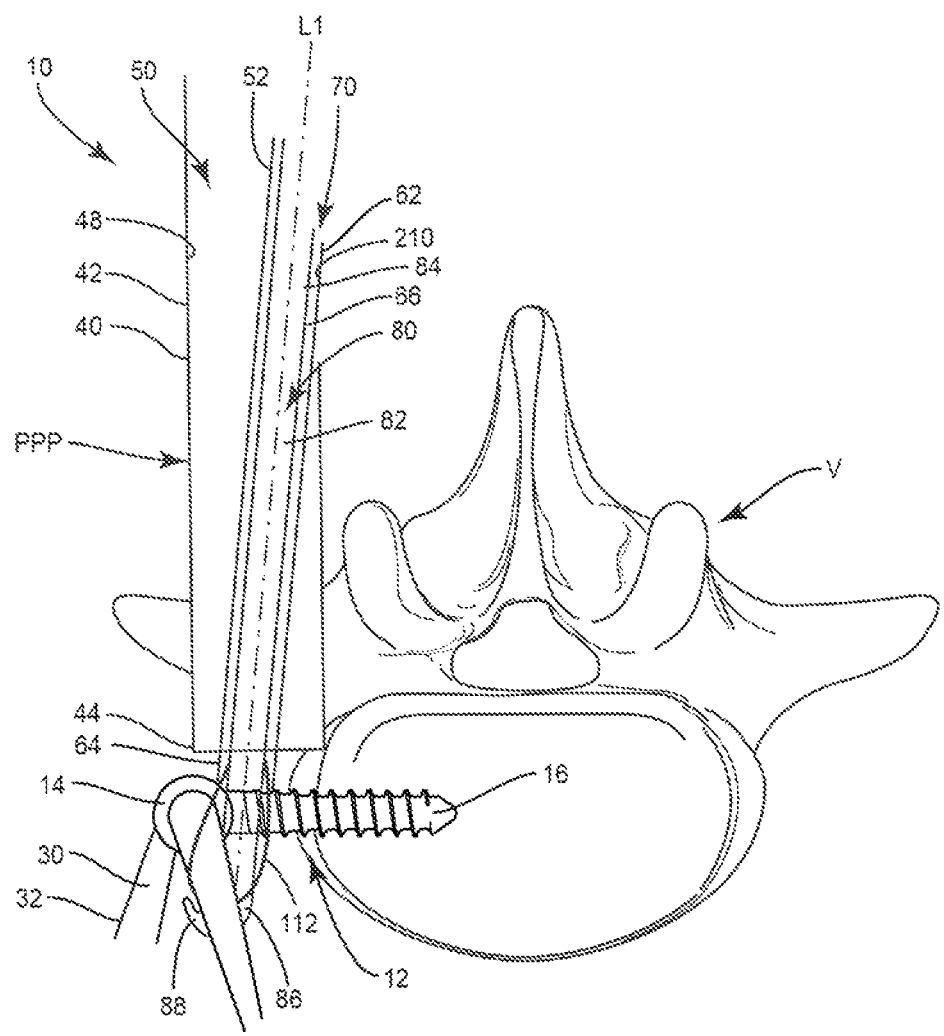
FIG. 5 is an axial view of components of one embodiment of a system in accordance with the principles of the present disclosure disposed with vertebrae.

System 10 includes a surgical instrument, such as, for example, a dilator 40. Dilator 40 is configured to dilate fascia and muscle fiber around the surgical site to create a posterior surgical pathway, such as, for example, a posterior percutaneous passageway PPP, as shown in FIG. 5, extending between a surface of the patient body to adjacent tether 30. In one embodiment, the tissue includes soft tissue adjacent a transverse process. In one embodiment, the tissue includes bony tissue adjacent the transverse process. Dilator 40 extends between a proximal end 42 and a distal end 44. In some embodiments, end 44 includes a tip configured to punch through fascia so fascia could then be expanded. Dilator 40 includes an inner surface 48 defining a passageway 50 configured to receive a surgical instrument or tool, such as, for example, those described herein.

System 10 includes a surgical instrument, such a cannula 52 having a circumferential cross section. Cannula 52 extends between an end 62 and an end 64. In one embodiment, end 62 may include a gripping surface 66 that may be such as, for example, rough, arcuate, undulating, mesh, porous, semi-porous, dimpled and/or textured. Cannula 52 includes an inner surface that defines a cavity 70 configured for disposal of the cutting instrument, as discussed herein. In one embodiment, dilator 40 includes cannula 52.

System 10 includes a surgical instrument, such as, for example a cutting instrument 80 configured for disposal in cavity 70. Cutting instrument 80 includes an elongated shaft 82 extending between an end 84 and an end 86 and defines a longitudinal axis L1. In one embodiment, end 84 may include a gripping surface that may be, such as, for example, rough, arcuate, undulating, mesh, porous, semi-porous, dimpled and/or textured to facilitate manipulation of cutting instrument 80. End 86 includes a cutting surface 88 that is hooked shaped. In some embodiments, cutting surface 88 may have various configurations such as, for example, round, oval, oblong, triangular, irregular, uniform or non-uniform.

Cutting surface 88 includes a cutting element, such as, for example, a cutting blade configured to cut and/or sever a longitudinal element, such as, for example, tether 30. In one embodiment, cutting surface 88 can be extended and retracted into cavity 70 to cut and/or sever tether 30. In one embodiment, cutting surface 88 may be guided via imaging guidance, as described herein.

Figure 4:
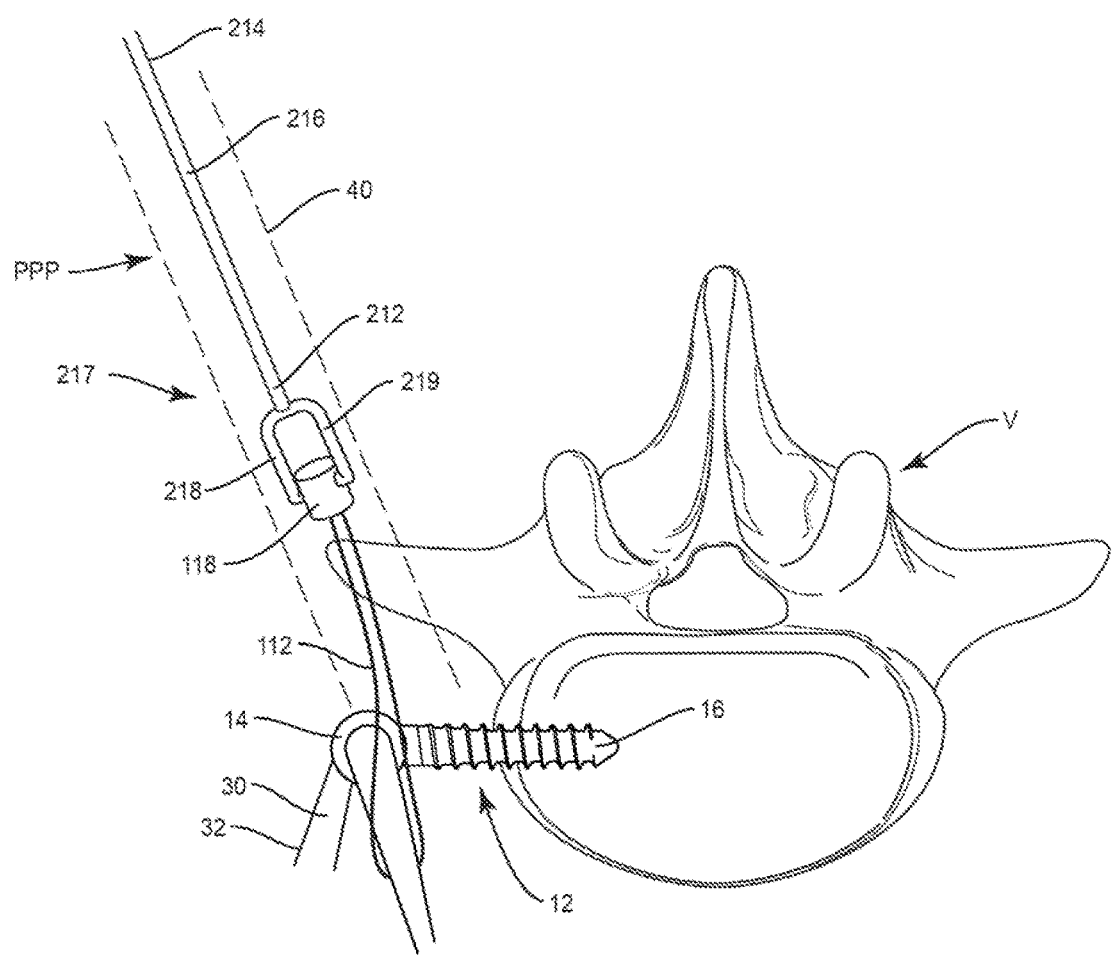
FIG. 4 is an axial view of the components and vertebrae shown in FIG. 3.

In assembly, operation and use, as shown in FIGS. 3-5, system 10, similar to the systems and methods described herein, is employed with and/or subsequent to a surgical correction procedure employing a surgical correction system, similar to those described herein. In some embodiments, system 10 may be employed concurrently with the surgical correction procedure. For example, the surgical correction system may be employed in surgical procedures for treating disorders of the spine, such as, for example, a correction treatment to treat child/adolescent idiopathic scoliosis and/or Scheuermann's kyphosis of a spine. In some embodiments, one or all of the components of system 10 can be delivered as a pre-assembled device or can be assembled in situ.

The surgical correction treatment includes a spinal construct including one or a plurality of detectable markers 108, similar to that described herein. Detectable markers 108 are attached with and spaced apart along tether 30. As such, detectable markers 108 are readily searchable and/or findable, for example, from a posterior approach using medical imaging. In some embodiments, the spinal construct including detectable markers 108 is implanted with vertebrae V in a prior surgical procedure. The spinal construct is used for correction and alignment for stabilization of a treated section of vertebrae V. Tether 30 is connected with heads 14 of bone screws 12 causing a tension in tether 30 and/or vertebrae V to displace, pull, twist or align vertebrae V as part of a correction system and treatment.

In use, to release tension and/or excessive or over correction of the implanted correction system, which includes tether 30 affixed with vertebrae V via bone screws 12, a medical practitioner obtains access to a surgical site including vertebrae V via a posterior surgical approach, as described herein. In some embodiments, the surgical site may be accessed in any appropriate manner, such as through incision and retraction of tissues. In some embodiments, system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area.

An incision is made in the body of a patient and a surgical pathway, such as, for example, pathway PPP is created adjacent the spinal construct, as described herein, for employment with system 10, as shown in FIG. 3. Dilator 40 is placed into the incision and inserted into pathway PPP from a posterior surface of the body of a patient and translated along tissue along a posterior approach such that distal end 44 is disposed adjacent a selected portion of the spinal construct, for example, a portion of tether 30. In some embodiments, dilator 40 is positioned via image guidance, such as, for example, computed tomography, fluoroscopy, magnetic resonance, positron emission tomography, ultrasound, or x-ray scans taken prior to or during the surgical procedure so as to minimize damage to tissue. For example, image guidance is provided to minimize damage to tissue surrounding a surgical site during placement of the components of system 10 and to aid in positioning dilator 40, cannula 52 and/or cutting instrument 80.

At least one of detectable markers 108 disposed with tether 30 is selectively detected and/or identified using medical imaging. In some embodiments, markers 108 may alternatively be selectively detected and/or identified using direct visual identification and/or tactile identification. Gripper 210 is disposed with passageway 50 and delivered through dilator 40 adjacent the selected portion of tether 30. Arms 218, 219 are disposed adjacent capture element 118 with loop 112 disposed about tether 30. Arms 218, 219 are manipulated such that extensions 220 engage mating cavities 126 for capture of detectable marker 108. Gripper 210 draws capture element 118 to release the reservoir of loop material disposed with capture element 118 such that loop 112 expands, as shown in FIG. 4. As such, capture element 118 is manipulated and tether 30 is drawn with loop 112 for accessing tether 30 to maneuver and/or manipulate tether 30. In some embodiments, marker 108 includes a substantially uniform outer surface, which does not include mating cavities, such that arms 218, 219 are manipulable to contact and capture the outer surface of marker 108. For example, a pituitary rongeur surgical instrument may be employed to contact and capture the outer surface of marker 108 to draw marker 108 in a posterior direction for accessing tether 30, as described herein.

Figure 6:
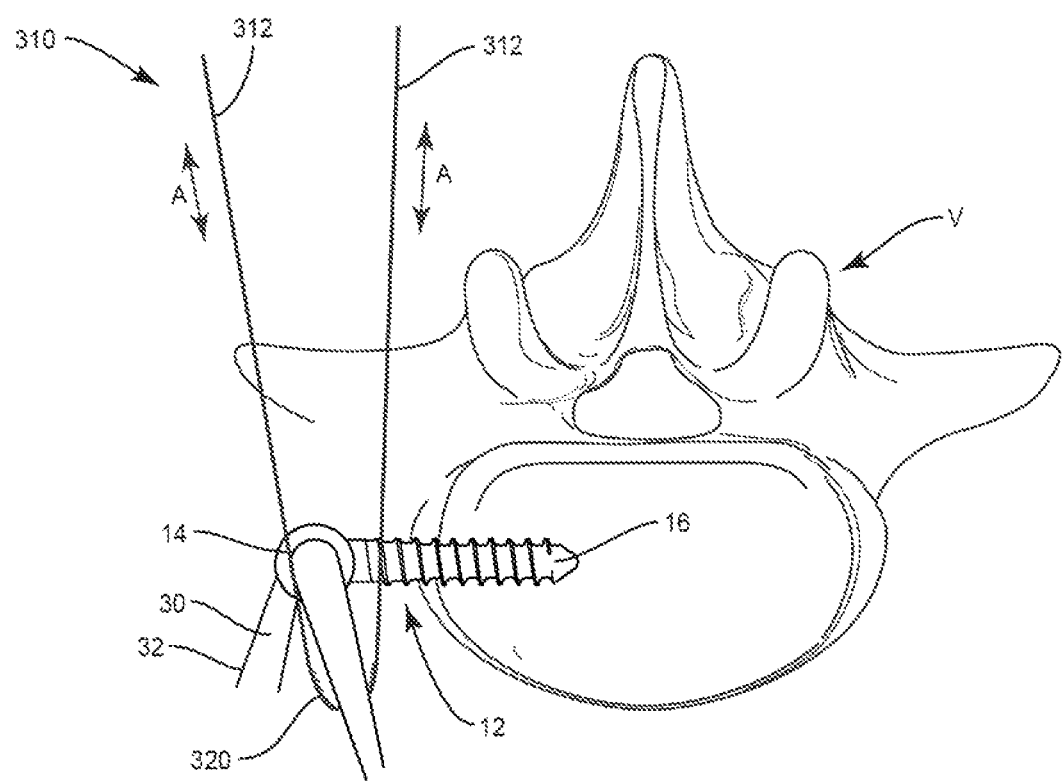
FIG. 6 is an axial view of components of one embodiment of a system in accordance with the principles of the present disclosure disposed with vertebrae.

Cutting instrument 80 is disposed with passageway 50 adjacent the selected portion of tether 30, as shown in FIG. 5. Cutting instrument 80 is positioned such that the blade of cutting surface 88 is disposed adjacent the portion of tether 30 to be cut. Manipulation of cutting instrument 80 causes the blade to cut tether 30 and release the tension in tether 30. In one embodiment, tether 30 is cut completely through its thickness. In one embodiment, tether 30 is cut only partially through its thickness. In one embodiment, as shown in FIG. 6, the cutting instrument comprises a flexible wire saw 310 for cutting and releasing the tension in tether 30. Wire saw 310 includes ends 312 and a serrated portion 320. In one embodiment, wire saw 312 is a gigli saw. In use, ends 312 are manipulated, in the directions shown by arrows A, such that portion 320 cuts tether 30 and releases the tension in tether 30.

Upon completion of a procedure, as described herein, the surgical instruments, assemblies and non-implanted components are removed from the surgical site and the incision(s) are closed. One or more of the components of system 10 can be made of radiolucent materials such as polymers. Radiopaque markers may be included for identification under x-ray, fluoroscopy, CT or other imaging techniques. In one embodiment, the detectable marker comprises a radiopaque loop. In some embodiments, the use of surgical navigation, microsurgical and image guided technologies may be employed to access, view or repair spinal aspects.

Figure 9:
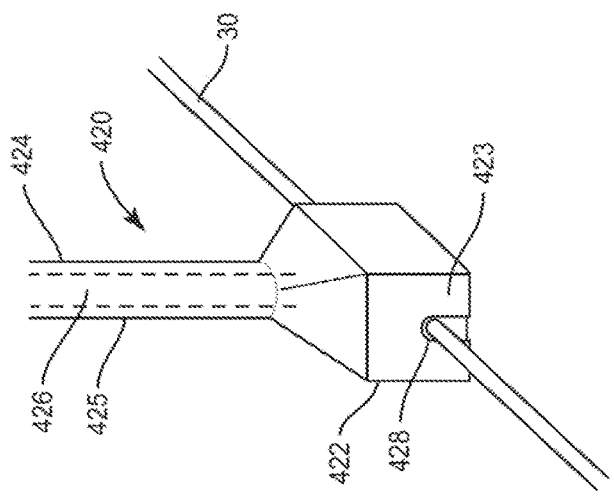
FIG. 9 is a perspective view of the components shown in FIG. 8.
Figure 8:
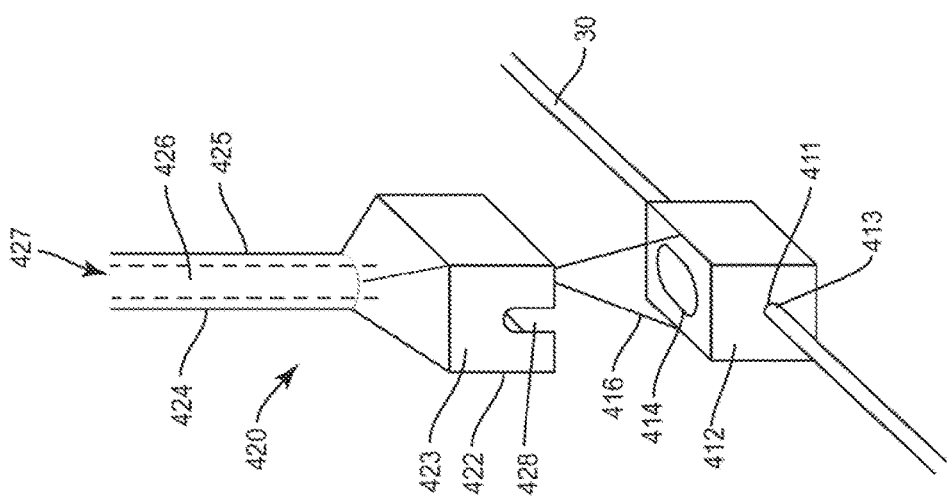
FIG. 8 is a perspective view of components of one embodiment of a system in accordance with the principles of the present disclosure.
Figure 7:
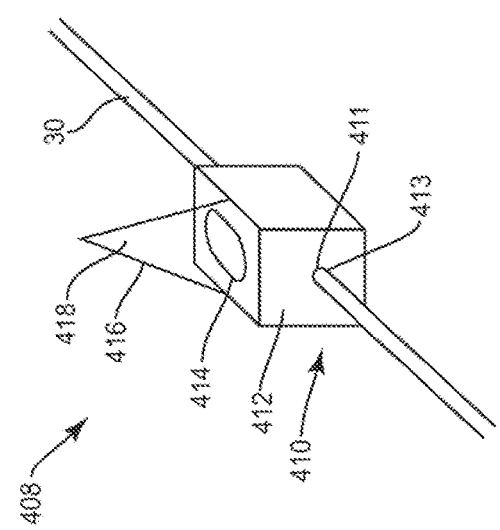
FIG. 7 is a perspective view of components of one embodiment of a system in accordance with the principles of the present disclosure.

In one embodiment, as shown in FIGS. 7-9, system 10, similar to the systems and methods described herein, includes a detectable marker 408, similar to detectable marker 108 described herein. Detectable marker 408 includes a housing 410 having a body 412 configured for disposal about a portion of tether 30, as shown in FIG. 7.

Body 412 has a cubical configuration and includes an inner surface 411 that defines a channel 413. Channel 413 extends through body 412 and is configured for disposal of tether 30. Surface 411 defines an opening 414 disposed in communication with channel 413 and configured to provide access for a surgical instrument, such as, for example, a cutting instrument, similar to those described herein, to tether 30.

Housing 410 comprises a capture element 416 configured for engagement with a surgical instrument, such as, for example, a hook (not shown) for capturing detectable marker 408. Capture element 416 is configured for disposal within a passageway 427 of a cannula 420, as shown in FIG. 8, for manipulation and/or maneuvering of tether 30 and/or cutting tether 30 to release the tension in tether 30. Capture element 416 includes a string, similar to string 109 described herein, that forms a loop 418 configured for engagement with the hook.

Capture element 416 is configured for engagement with cannula 420, which includes an elongated portion 425 extending between a distal end 422 and a proximal end 424. Elongated portion 425 comprises inner surface 426 defining passageway 427, which is configured to allow passage of a surgical instrument, such as, for example, a cutting instrument. End 422 comprises a housing 423 having an opening configured to receive housing 410. Housing 410 is disposed within housing 423 such that passageway 427 is in communication with opening 414. Housing 423 defines a pair of U-shaped apertures 428 configured for disposal about tether 30, as shown in FIG. 9.

In use, cannula 420 is disposed adjacent detectable marker 408, which is connected with tether 30, at a surgical site. The hook is disposed with passageway 427 and delivered therethrough adjacent the selected portion of tether 30. The hook is disposed adjacent capture element 416 with loop 418 disposed about tether 30. The hook captures loop 418 for capture of detectable marker 408. The hook draws loop 418 such that tether 30 is drawn with housing 410 for accessing tether 30 to maneuver and/or manipulate tether 30.

The cutting instrument is disposed with passageway 427 adjacent the selected portion of tether 30. The cutting instrument is disposed adjacent the portion of tether 30 to be cut, as described herein. Manipulation of the cutting instrument causes cutting of tether 30 and release of the tension in tether 30.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant detection device comprising:
at least one detectable marker connectable to an implantable longitudinal element and including a capture element configured to facilitate manipulation of the longitudinal element, the capture element comprising a housing comprising opposite top and bottom surfaces and a sidewall that extends from the top surface to the bottom surface, the at least one detectable marker including a loop, the loop comprising opposite ends extending through the bottom surface such that the ends are positioned within the housing without extending through the sidewall,
wherein the housing is free of any openings that extend through the top surface.

2. A device as recited in claim 1, wherein the loop is configured to be disposed about the longitudinal element.

3. A device as recited in claim 1, wherein the loop is expandable.

4. A device as recited in claim 1, herein the loop is radiopaque.

5. A device as recited in claim 1, wherein the loop is configured to be disposed about the longitudinal element and connected with the capture element, the capture element comprising a cap engageable with a surgical instrument.

6. A device as recited in claim 1, wherein the housing is configured to be disposed about the longitudinal element.

7. A device as recited in claim 6, wherein the housing comprises a cylindrical configuration.

8. A device as recited in claim 1, wherein the housing comprises an inner surface that is configured to connect with the ends of the loop.

9. A device as recited in claim 1, wherein the longitudinal element is implantable with an anterior portion of vertebrae and the capture element is configured for capture along a posterior surgical pathway.

10. A device as recited in claim 1, wherein the longitudinal element is implantable with an anterior portion of vertebrae and the capture element is configured for disposal adjacent a posterior portion of the vertebrae.

11. A device as recited its claim 1, wherein the at least one detectable marker comprises visual indicia.

12. A device as recited in claim 1, wherein the at least one detectable marker comprises tactile indicia.

13. A device as recited in claim 1, wherein the at least one detectable marker comprises a radio frequency identification device.

14. A device as cited in claim 1, wherein the longitudinal element includes a tether.

15. A device as recited in claim 1, wherein the longitudinal element includes a tether that is configured to be implanted with an anterior portion of vertebrae.

16. A device as cited in claim 1, wherein the housing comprises a pair of mating cavities that extend through an outer surface of the sidewall.

17. A device as cited in claim 1, wherein the ends each include a reservoir of loop material disposed within the housing such that the loop is expandable.

18. A device as cited in claim 1, wherein end surfaces of the ends are positioned within the housing.

19. A device as cited in claim 1, wherein the loop has elastic properties.

20. A detectable marker comprising:
a housing comprising opposite top and bottom surfaces and a sidewall that extends from the top surface to the bottom surface; and
a string comprising opposite ends extending through the bottom surface such that the end surfaces of the ends are positioned within the housing, the string forming a loop that is movable between a first configuration in which the ends are coiled within the housing and the loop has a first length and a second configuration in which the ends are uncoiled within the housing and the loop has a second length that is greater than the first length.

21. A detectable marker comprising:
a housing having a cylindrical configuration, the housing comprising opposite top and bottom surfaces and a sidewall that extends from the top surface to the bottom surface, the housing comprising a pair of mating cavities that extend through an outer surface of the sidewall, the housing being free of any openings that extend through the top surface; and
a loop, the loop comprising opposite ends extending through the bottom surface such that the ends are positioned within the housing without extending through the sidewall, the loop being movable between a first configuration in which the ends are coiled within the housing and the loop has a first length and a second configuration in which the ends are uncoiled within the housing and the loop has a second length that is greater than the first length.

* * * * *

UNITED STATES PATENT AND TRADEMARK OFFICE
CERTIFICATE OF CORRECTION

PATENT NO.       : 9,693,809 B2                                  Page 1 of 1
APPLICATION NO.  : 14/221051
DATED            : July 4, 2017
INVENTOR(S)      : Schwab It is certified that error appears in the above-identified patent and that said Letters Patent is hereby corrected as shown below:

In the Specification

In Column 2, Line 24, delete "which" and insert -- which are --, therefor.

In Column 4, Lines 57-58, delete "inducting" and insert -- including --, therefor.

In Column 6, Line 12, delete "rape," and insert -- rope, --, therefor.

In Column 7, Line 5, delete "same" and insert -- some --, therefor.

In Column 9, Line 23, delete "wire saw 312" and insert -- wire saw 310 --, therefor.

In the Claims

In Column 11, Line 1, in Claim 11, delete "its claim" and insert -- in claim --, therefor.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*